United States Patent
Laufer

(10) Patent No.: US 11,447,447 B2
(45) Date of Patent: Sep. 20, 2022

(54) METHOD FOR PRODUCING CARBODIIMIDES

(71) Applicant: LANXESS Deutschland GmbH, Cologne (DE)

(72) Inventor: Wilhelm Laufer, Ellerstadt (DE)

(73) Assignee: LANXESS Deutschland GmbH, Cologne (DE)

( * ) Notice: Subject to any disclaimer, the term of this patent is extended or adjusted under 35 U.S.C. 154(b) by 0 days.

(21) Appl. No.: 16/956,179

(22) PCT Filed: Dec. 17, 2018

(86) PCT No.: PCT/EP2018/085127
§ 371 (c)(1),
(2) Date: Jun. 19, 2020

(87) PCT Pub. No.: WO2019/121462
PCT Pub. Date: Jun. 27, 2019

(65) Prior Publication Data
US 2020/0331849 A1 Oct. 22, 2020

(30) Foreign Application Priority Data

Dec. 20, 2017 (EP) .................................... 17209011
Dec. 28, 2017 (EP) .................................... 17210799

(51) Int. Cl.
*C07C 267/00* (2006.01)
*C08G 18/79* (2006.01)
*C07C 263/16* (2006.01)
*C07C 263/18* (2006.01)

(52) U.S. Cl.
CPC .......... *C07C 267/00* (2013.01); *C07C 263/16* (2013.01); *C07C 263/18* (2013.01); *C08G 18/797* (2013.01)

(58) Field of Classification Search
CPC ... C07C 267/00; C07C 263/16; C07C 263/18; C08G 18/797
See application file for complete search history.

(56) References Cited

U.S. PATENT DOCUMENTS

| 5,434,305 A | 7/1995 | Hennig et al. |
| 9,434,807 B2 | 9/2016 | Laufer et al. |

FOREIGN PATENT DOCUMENTS

| DE | 1130594 B | 5/1962 | |
| EP | 0602477 A1 * | 6/1994 | ........... C07C 267/00 |

OTHER PUBLICATIONS

International Search Report from corresponding International Application No. PCT/EP2018/085127, dated Mar. 8, 2019, two pages.
Wagner, Kuno et al., "α,ω-Diisocyanatocarbodiimides, -Polycarbodiimides, and Their Derivatives", Angew. Chem. 1981, 93, 855-866, Abstract, obtained from the Internet on May 4, 2021, at www.https://onlinelibrary.wiley.com/doi/10.1002/anie.198108193.
Rahmana, A.K., et al., "Catalytic conversion of isocyanates to carbodiimides by cyclopentadienyl manganese tricarbonyl and cyclopentadienyl iron dicarbonyl dimer", Tetrahedron Letters 48 (2007) 6002-6004, Elsevier, obtained from the Internet on May 4, 2021, at www.sciencedirect.com.
Neumann, Wolfram, et al. "Carbodiimide aus Isocyanaten", Angew. Chem. 1962, 74, Issue 21, 801-806 Translation of Abstract with article, obtained from the Internet on May 11, 2021 at www.https://onlinelibrary.wiley.com/doi/abs/10.1002/ange.19620742104.

* cited by examiner

*Primary Examiner* — Rabon A Sergent
(74) *Attorney, Agent, or Firm* — Nicanor A. Kohncke; Christopher L. McDavid; Ewa M. Wozniak

(57) ABSTRACT

The present disclosure provides new methods for preparing carbodiimides including steps of carbodiimidizing monomeric aromatic isocyanates in the presence of a catalyst, separating low boilers and catalyst from the reaction product in a thin-film evaporator, and distilling the residue from the thin-film evaporation in a further thin-film evaporator.

11 Claims, No Drawings

METHOD FOR PRODUCING CARBODIIMIDES

The invention relates to a novel method for preparing carbodiimides, preferably monomeric, sterically hindered aromatic carbodiimides. Carbodiimides have proven useful in many applications, for example as hydrolysis inhibitors for thermoplastics, polyols, polyurethanes, triglycerides and lubricating oils, etc.

The prior art synthesis of carbodiimides starts from isocyanates, which are carbodiimidized under basic or heterocyclic catalysis with elimination of $CO_2$. This allows mono- or polyfunctional isocyanates to be converted into monomeric or polymeric carbodiimides.

The catalysts typically used are alkali metal or alkaline earth metal compounds and also heterocyclic compounds containing phosphorus, see Angew. Chem. 1962, 74, 801-806 and Angew. Chem. 1981, 93, 855-866.

The complete removal of the phosphorus-containing catalyst that is normally used is difficult. Since carbodiimides are used by preference in the production of polyurethanes, the presence of even traces of phosphorus causes severe problems and must therefore be avoided. Furthermore, the monomeric carbodiimides prepared should have a color index that is as low as possible and a low isocyanate content, which is industrially achievable usually only by distillations or multiple crystallizations involving losses of yield or by a laborious reaction in the presence of $CO_2$, see EP-A 0 602 477 and EP-A 2 855 573.

It was therefore an object of the present invention to provide an improved method for preparing certain monomeric carbodiimides that allows them to be prepared with a low color index; these monomeric carbodiimides should ideally be free of organophosphorus compounds and unreacted starting materials, preferably isocyanates, so that they may then be used in the production and/or stabilization of PU systems.

It has now been surprisingly found that these abovementioned objects are achieved when the method is carried out in the following steps:
  carbodiimidizing monomeric aromatic isocyanates in the presence of a catalyst,
  separating the low boilers and catalyst from the reaction product in a thin-film evaporator, and
  distilling the residue in a further thin-film evaporator.

The present invention thus provides a method for preparing monomeric aromatic carbodiimides that is carried out in the following steps:
  carbodiimidizing monomeric aromatic isocyanates in the presence of a catalyst,
  separating the low boilers and catalyst from the reaction product in a thin-film evaporator, and
  distilling the residue in a further thin-film evaporator.

Monomeric aromatic carbodiimides in the context of the invention are carbodiimides bearing $C_1$-$C_6$ alkyl- and/or $C_1$-$C_6$ alkoxy-substituted phenyl radicals that are directly bonded to the nitrogen of the carbodiimide group via a carbon atom of the phenyl radical or via an alkyl group on the phenyl radical.

Particular preference is given here to monomeric carbodiimides of the formula (I)

$$R—N=C=N—R^1 \quad (I)$$

where R and also $R^1$ are

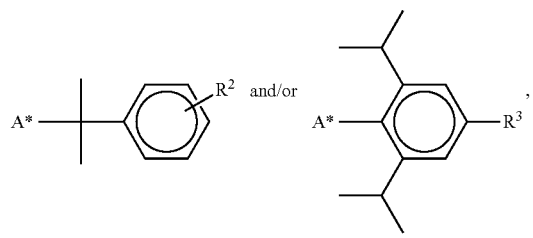

$R^2$=isopropenyl, t-butyl or $C_1$-$C_6$ alkoxy,
$R^3$=H, methyl, ethyl, isopropyl, n-propyl and/or tert-butyl, preferably methyl, ethyl, isopropyl, n-propyl and/or tert-butyl,
and A* represents the linkage to the nitrogen of the carbodiimide function in formula (I).

For the preferred carbodiimides of the formula (I), the method of the invention is effected by
a) reacting (carbodiimidizing) isocyanates selected from the group R—N=C=O and/or $R^1$—N=C=O, where R and $R^1$ are as defined above, in the presence of a catalyst,
b) separating the low boilers and catalyst from the reaction product from a) in a thin-film evaporator, and
c) distilling the residue from b) in a further thin-film evaporator.

In a preferred embodiment of the present method, the carbodiimide corresponds to a compound of the formula (II)

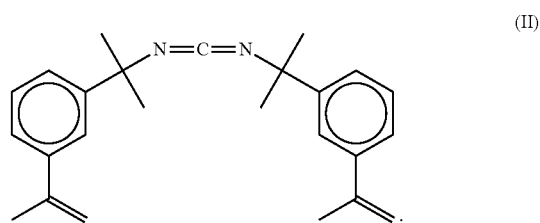

(II)

In a further preferred embodiment of the method of the invention, the carbodiimide corresponds to a compound of the formula (I) R—N=C=N—$R^1$, where R and $R^1$ are

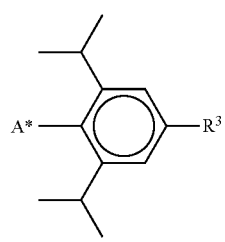

$R^3$ is an isopropyl radical, and A* represents the linkage to the nitrogen of the carbodiimide function in formula (I).

The carbodiimidization of isocyanates in the presence of a catalyst in step a) in the context of the method of the invention is effected in a condensation reaction with elimination of $CO_2$, as described, for example, in the in Angew. Chem. 93, pp. 855-866 (1981) or DE-A-11 30 594 or Tetrahedron Letters 48 (2007), pp. 6002-6004.

The carbodiimidization can be carried out with or without solvent. It is likewise possible to begin the carbodiimidization without solvent and then for this to be completed after addition of a solvent. Preference is given to using benzines, benzene and/or alkylbenzenes as solvent.

The isocyanate used is preferably 3-isopropenyl-α,α-dimethylbenzyl isocyanate (TMI) and/or 2,4,6 triisopropylphenyl isocyanate (TRIPI).

In one embodiment of the invention, the catalysts for preparing compounds of the formula (I) are preferably phosphorus compounds. Preference is given to using phospholene oxides, phospholidines or phosphoncoline oxides and also the corresponding sulfides. The catalyst is particular preferably an alkylphospholene oxide where alkyl=$C_1$-$C_6$ alkyl, preferably methylphospholene oxide.

The reaction is preferably carried out within a temperature range of 40° C. to 200° C.

In a further preferred embodiment of the method of the invention, the carbodiimidization is followed by a filtration of the reaction product from a). If a filtration is carried out, this is preferably done using a filter cartridge or bag filter, optionally with the addition of filtration aids such as preferably diatomaceous earth or activated carbon.

The filtration is preferably carried out at temperatures of 30 to 100° C.

After the carbodiimidization a) and optional filtration, low boilers and catalyst are separated from the reaction product from a) in a thin-film evaporator.

The thin-film evaporator in the context of the invention is an evaporator that evaporates liquids in a thin film. It is preferably operated under reduced pressure and is therefore suitable for the separation of substance mixtures under mild conditions. Among thin-film evaporators in the context of the invention, preference is given to falling-film evaporators having rotating wipers, as obtainable for example from VTA GmbH & Co. KG.

Low boilers in the context of the invention are preferably by-products or unreacted reactants/isocyanates resulting from performance of the carbodiimidization that have boiling points at least 50° C., preferably at least 60° C., more preferably at least 70° C., below that of the monomeric carbodiimide that has been prepared or of the corresponding carbodiimide mixture.

The separation in step b) is preferably carried out at a temperature of 150° C. to 200° C., preferably 160° C. to 190° C., more preferably 170° C. to 180° C., and at a pressure of 0.1 to 5 mbar, preferably 0.2-1 mbar, more preferably 0.3-0.6 mbar.

In a further preferred embodiment of the invention, the temperature difference between step b) and step c) is 5° C., preferably 10° C.

In a further preferred embodiment of the invention, the temperature in step c) is 5° C. higher, preferably 10° C. higher, than in step b).

In a further embodiment, so-called entraining agents can be used in the removal of the low boilers. Preference is given here to $C_1$-$C_{12}$ alkyl-substituted benzenes and/or dibenzenes and/or pyrrolidones. N-methyl- and N-ethylpyrrolidone and/or xylene are preferred for this.

In step c), the residue from b) is distilled in a further thin-film evaporator. The distillation of the residue from c) is preferably carried out in a further thin-film evaporator. The thin-film evaporator used is preferably a short-path evaporator.

Short-path evaporators in the context of the invention are modified thin-film evaporators in which the condenser is integrated inside the evaporator cylinder. This means that the path the vapor has to travel from the product film to the condenser is very short.

The residue from b) in the context of the invention predominantly comprises the monomeric carbodiimides that have been prepared and resulting by-products.

In step c), the distillation of the residue from b) is preferably carried out at a temperature of 160° C. to 220° C., preferably 165° C. to 210° C., more preferably 190° C. to 205° C., and at a pressure of 0.05 to 5 mbar, preferably 0.1-1 mbar, more preferably 0.2-0.6 mbar.

In a further preferred embodiment of the invention, steps b) and c) are carried out continuously without isolating the residue from b).

The monomeric carbodiimides prepared by the method of the invention preferably have a color index of <10 in the b value, measured according to CIE L*a*b* in accordance with ISO 11664-4, in combination with small amounts of monomeric isocyanate of <0.1% and a phosphorus content of <1 ppm.

The present invention further provides for the use of the monomeric carbodiimides prepared by the method of the invention in the production of hydrolysis-stable polyurethane-based (PU-based) systems, preferably thermoplastic polyurethane (TPU), soft and rigid PU foam, and hot-cast PU elastomers.

The scope of the invention encompasses all radical definitions, indices, parameters and elucidations mentioned above and detailed hereinafter, in general terms or within preferred ranges, together with one another, i.e. including the respective ranges and preferred ranges in any combination.

The examples that follow serve to elucidate the invention, without being limiting.

WORKING EXAMPLES

CDI 1: 2,6-Diisopropylphenylcarbodiimide
CDI 2: Carbodiimide of the formula (II)

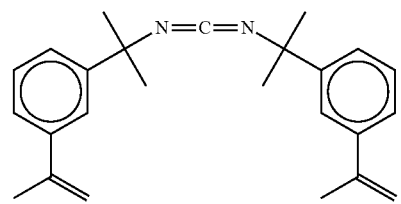

CDI 3: Carbodiimide of the formula (I) R—N=C=N—$R^1$, where R and $R^1$ represent

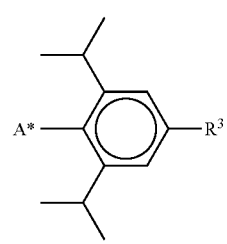

and $R^3$ is an isopropyl radical and where A* represents the linkage to the nitrogen of the carbodiimide function in formula (I).

Carbodiimidization

The carbodiimides CDI 1 to 3 were prepared in a stainless steel tank through the reaction of the corresponding isocyanates, i.e. 2,6-diisopropylphenyl isocyanate (DIPPI) was used for CDI 1, 3-isopropenyl-α,α-dimethylbenzyl isocyanate (TMI) for CDI 2, and 2,4,6-triisopropylphenyl isocyanate (TRIPI) for CDI 3, in the presence of 200-500 ppm methylpholene oxide as catalyst at temperatures of 160-170° C. with elimination of $CO_2$. The carbodiimidization reaction was continued until a residual isocyanate content of <1% was reached.

The carbodiimides CDI 1 to CDI 3 thus prepared were then fed into the distillations described below.

a) Distillation and distillation in a thin-film evaporator (comparison) according to EP-A-0 602 477:

The carbodiimides CDI 1 to 3 were first separated from the low boilers in a batchwise process at approx. 200-220° C. and a pressure of 0.3-0.4 mbar using a Vigreux column and then continuously distilled in a VTA thin-film evaporator at temperatures of 190-200° C. and a pressure of 0.4 mbar.

b) Distillation using 2 thin-film evaporators (inventive):

The carbodiimides CDI 1 to 3 were first freed of low boilers in a VTA thin-film evaporator at temperatures of 160-170° C. and a pressure of 1.0 mbar and the residue was distilled in a second thin-film evaporator identical to the first at temperatures of 200-205° C. and a pressure of 0.4 mbar.

The color was determined by the CIE L*a*b* method in accordance with ISO 11664-4. The b* value was evaluated.

The residual content of monomeric isocyanate was determined by HPLC and the phosphorus content by X-ray fluorescence analysis (XRF).

The results are shown in table 1 below.

TABLE 1

| CDI | Distillation + distillation in a thin-film evaporator (comp.) | | | 2 thin-film evaporators (inv.) | | |
|---|---|---|---|---|---|---|
| | Color, b* | Content of monomeric isocyanate (%) | Phosphorus content (ppm) | Color, b* | Content of monomeric isocyanate (%) | Phosphorus content (ppm) |
| CDI 1 | 10-12 | >0.1 | 4-5 | 2-3 | >0.1 | 3 |
| CDI 2 | 5-6 | >0.1 | 10-12 | 0-1 | <0.1 | <1** |
| CDI 3 | 30-40 | >0.1 | 5-6 | 8-9 | <0.1 | <1** | comp. = comparison
inv. = inventive
**Below the detection limit of 1 ppm

The carbodiimides CDI 1 to CDI 3 prepared by the method of the invention have improved properties compared to those prepared by the prior art method.

As can be seen from table 1, the preferred carbodiimides CDI 2 and CDI 3 in particular can be prepared in particularly high quality, i.e. low color index, low content of toxic monomeric isocyanate and, moreover, having no detectable content of organophosphorus compounds.

These are ideally suited for use in the production and/or stabilization of PU systems.

What is claimed is:

1. A method for preparing monomeric aromatic carbodiimides, the method comprising:
    a) carbodiimidizing monomeric aromatic isocyanates in the presence of a catalyst,
    b) separating low boilers and catalyst from the reaction product from a) in a thin-film evaporator leaving a residue comprising monomeric carbodiimides and byproducts from the carbodiimidization, and
    c) distilling the residue from b) in a further thin-film evaporator.

2. The method as claimed in claim 1, wherein the monomeric aromatic carbodiimides are carbodiimides of the formula (I)

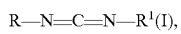

where R and $R^1$ are chosen from

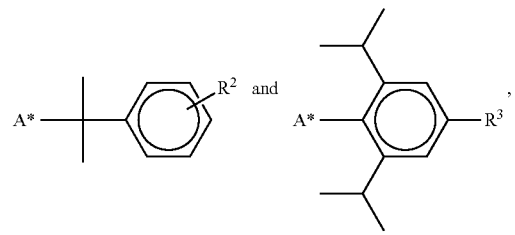

$R^2$=isopropenyl, t-butyl or $C_1$-$C_6$ alkoxy, $R^3$=H, methyl, ethyl, isopropyl, n-propyl or tert-butyl, and A* represents the linkage to the nitrogen of the carbodiimide function in formula (I).

3. The method as claimed in claim 2, wherein the carbodiimide of the formula (I) corresponds to

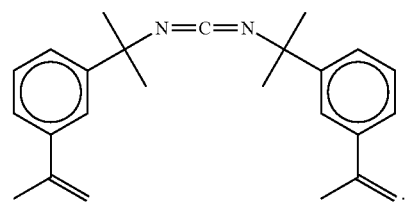

4. The method as claimed in claim 1, wherein the distillation steps b) and c) are operated as a continuous process.

5. The method as claimed in claim 1, wherein the distillation in step b) is carried out at a temperature of 150° C. to 220° C. and at a pressure of 0.1 to 5 mbar.

6. The method as claimed in claim 1, wherein in step b) $C_1$-$C_{12}$ alkyl-substituted benzenes, dibenzenes and/or pyrrolidones are used as entraining agents in the removal of low boilers.

7. The method as claimed in claim 1, wherein the distillation step c) is performed at a temperature 5° C. higher or 10° C. higher than in step b).

8. The method as claimed in claim 1, wherein the distillation in step c) is carried out at a temperature of 160° C. to 220° C. and at a pressure of 0.05 to 5 mbar.

9. The method as claimed in claim 1, wherein the isocyanate used is 3-isopropenyl-α,α-dimethyl benzyl isocyanate (TMI) and/or 2,4,6-triisopropylphenyl isocyanate (TRIPI).

10. The method as claimed in claim 1, wherein the thin-film evaporator used in step c) is a short-path evaporator.

11. A method of producing a hydrolysis-stable polyurethane-based system, comprising adding to the system monomeric aromatic carbodiimides prepared according to the method of claim 1.

* * * * *